(12) United States Patent
Mannanal et al.

(10) Patent No.: US 11,974,781 B2
(45) Date of Patent: May 7, 2024

(54) GEAR MECHANISMS FOR FIXATION FRAME STRUTS

(71) Applicant: Stryker European Operations Holdings LLC, Kalamazoo, MI (US)

(72) Inventors: Subash K. Mannanal, Mahwah, NJ (US); Daniel Greenberg, Ramsey, NJ (US); Patrick Valli, Brookside, NJ (US); Manoj Kumar Singh, Mahwah, NJ (US); Cem Adalioglu, Mönkeberg (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 56 days.

(21) Appl. No.: 18/046,910

(22) Filed: Oct. 15, 2022

(65) Prior Publication Data

US 2023/0065111 A1 Mar. 2, 2023

Related U.S. Application Data

(63) Continuation of application No. 17/006,979, filed on Aug. 31, 2020, now Pat. No. 11,504,160, which is a continuation of application No. 15/948,219, filed on Apr. 9, 2018, now abandoned, which is a continuation of application No. 15/181,614, filed on Jun. 14, 2016, now Pat. No. 10,010,350.

(51) Int. Cl.
*A61B 17/66* (2006.01)
*A61B 17/62* (2006.01)

(52) U.S. Cl.
CPC .............. *A61B 17/66* (2013.01); *A61B 17/62* (2013.01)

(58) Field of Classification Search
CPC .............................................. A61B 17/60–666
See application file for complete search history.

(56) References Cited

U.S. PATENT DOCUMENTS

| 2,055,024 A | 9/1936 | Bittner, Jr. |
| 2,250,417 A | 7/1941 | Ettinger |

(Continued)

FOREIGN PATENT DOCUMENTS

| DE | 3439795 A1 | 6/1985 |
| DE | 3729253 A1 | 3/1989 |

(Continued)

*Primary Examiner* — Eduardo C Robert
*Assistant Examiner* — Steven J Cotroneo
(74) *Attorney, Agent, or Firm* — SLEMAN & LUND LLP

(57) ABSTRACT

An adjustable length strut includes two joints, a threaded rod extending between the joints, and a tube adapted to receive the threaded rod. An actuation mechanism with gear teeth extending radially outward of the strut axis is rotatably fixed to the threaded rod. A protrusion may be coupled to an end of the threaded rod by a rotatable collar, with the protrusion extending through a slot in the tube to mark the length of the strut. A modular attachment member may be adapted to be couple to the first joint and include a worm gear adapted to engage gear teeth of the actuation mechanism. The modular attachment member may include a radiofrequency identity tag mechanism adapted to be read by a tag reader of a tool, the tool adapted to couple to the attachment member to rotate the worm gear to increase or decrease the effective length of the strut.

20 Claims, 12 Drawing Sheets

(56) References Cited

U.S. PATENT DOCUMENTS

| | | | |
|---|---|---|---|
| 2,333,033 A | 10/1943 | Mraz | |
| 2,391,537 A | 12/1945 | Anderson | |
| 2,393,831 A | 1/1946 | Stader | |
| 2,406,987 A | 9/1946 | Anderson | |
| 2,432,695 A | 12/1947 | Speas | |
| 3,727,610 A | 4/1973 | Riniker | |
| 3,866,607 A | 2/1975 | Forsythe | |
| 3,941,123 A | 3/1976 | Volkov | |
| 3,975,032 A | 8/1976 | Bent | |
| 3,977,397 A | 8/1976 | Kalnberz | |
| 3,985,127 A | 10/1976 | Volkov | |
| 4,006,740 A | 2/1977 | Volkov | |
| 4,033,340 A | 7/1977 | Kalnberz | |
| 4,091,880 A | 5/1978 | Troutner | |
| 4,100,919 A | 7/1978 | Oganesyan | |
| 4,112,935 A | 9/1978 | Latypov | |
| 4,308,863 A * | 1/1982 | Fischer | A61B 17/62 606/56 |
| 4,312,336 A | 1/1982 | Danieletto | |
| 4,338,927 A | 7/1982 | Volkov | |
| 4,365,624 A | 12/1982 | Jaquet | |
| 4,450,834 A | 5/1984 | Fischer | |
| 4,488,542 A | 12/1984 | Helland | |
| 4,535,763 A | 8/1985 | Jaquet | |
| 4,554,915 A | 11/1985 | Brumfield | |
| 4,570,625 A | 2/1986 | Harris | |
| 4,607,625 A | 8/1986 | Schenck | |
| 4,615,338 A * | 10/1986 | Ilizarov | A61B 17/62 606/58 |
| 4,624,249 A | 11/1986 | Alvarez Cambras | |
| 4,768,524 A | 9/1988 | Hardy | |
| 4,784,125 A | 11/1988 | Monticelli | |
| 4,889,111 A | 12/1989 | Ben-Dov | |
| 4,890,631 A | 1/1990 | Hardy | |
| 4,923,458 A | 5/1990 | Fischer | |
| 4,936,843 A | 6/1990 | Sohngen | |
| 4,964,320 A | 10/1990 | Lee, Jr. | |
| 4,973,331 A | 11/1990 | Pursley | |
| 4,978,347 A | 12/1990 | Ilizarov | |
| 5,028,180 A | 7/1991 | Sheldon | |
| 5,062,844 A | 11/1991 | Jamison | |
| 5,067,954 A | 11/1991 | Ilizarov | |
| 5,087,258 A | 2/1992 | Schewior | |
| 5,102,411 A | 4/1992 | Hotchkiss | |
| 5,108,394 A | 4/1992 | Kurokawa | |
| 5,129,898 A | 7/1992 | Brusasco | |
| 5,156,605 A | 10/1992 | Pursley | |
| 5,180,380 A * | 1/1993 | Pursley | A61B 17/7216 606/56 |
| 5,207,676 A | 5/1993 | Canadell | |
| 5,275,598 A | 1/1994 | Cook | |
| 5,312,410 A | 5/1994 | Miller | |
| 5,314,426 A | 5/1994 | Pohl | |
| 5,334,202 A | 8/1994 | Carter | |
| 5,431,659 A | 7/1995 | Ross, Jr. | |
| 5,437,668 A | 8/1995 | Aronson | |
| 5,443,464 A | 8/1995 | Russell | |
| 5,451,225 A | 9/1995 | Ross, Jr. | |
| 5,496,319 A | 3/1996 | Allard | |
| 5,540,686 A | 7/1996 | Zippel | |
| 5,601,551 A * | 2/1997 | Taylor | A61B 17/66 606/53 |
| 5,630,814 A | 5/1997 | Ross, Jr. | |
| 5,643,319 A | 7/1997 | Green | |
| 5,649,927 A | 7/1997 | Kilpela | |
| 5,662,648 A | 9/1997 | Faccioli | |
| 5,676,664 A | 10/1997 | Allard | |
| 5,681,309 A * | 10/1997 | Ross, Jr. | A61B 17/62 606/56 |
| 5,688,271 A | 11/1997 | Faccioli | |
| 5,700,263 A | 12/1997 | Schendel | |
| 5,702,389 A | 12/1997 | Taylor | |
| 5,713,897 A | 2/1998 | Goble | |
| 5,725,526 A | 3/1998 | Allard | |
| 5,728,095 A | 3/1998 | Taylor | |
| 5,741,252 A | 4/1998 | Mazzio | |
| 5,746,741 A | 5/1998 | Kraus | |
| 5,766,173 A | 6/1998 | Ross, Jr. | |
| 5,776,132 A | 7/1998 | Blyakher | |
| 5,788,695 A | 8/1998 | Richardson | |
| 5,797,908 A | 8/1998 | Meyers | |
| 5,843,081 A | 12/1998 | Richardson | |
| 5,863,292 A | 1/1999 | Tosic | |
| 5,870,834 A | 2/1999 | Sheldon | |
| 5,885,282 A | 3/1999 | Szabo | |
| 5,891,143 A | 4/1999 | Taylor | |
| 5,902,306 A | 5/1999 | Norman | |
| 5,919,192 A | 7/1999 | Shouts | |
| 5,928,230 A | 7/1999 | Tosic | |
| 5,928,234 A | 7/1999 | Manspeizer | |
| 5,931,837 A | 8/1999 | Marsh | |
| 5,968,043 A | 10/1999 | Ross, Jr. | |
| 5,971,984 A | 10/1999 | Taylor | |
| 5,976,133 A | 11/1999 | Kraus | |
| 5,976,136 A | 11/1999 | Bailey | |
| 5,997,537 A | 12/1999 | Walulik | |
| 6,017,341 A | 1/2000 | Windhagen | |
| 6,021,579 A | 2/2000 | Schimmels | |
| 6,030,386 A * | 2/2000 | Taylor | A61B 17/62 606/56 |
| 6,033,412 A | 3/2000 | Losken | |
| 6,036,691 A | 3/2000 | Richardson | |
| 6,042,585 A | 3/2000 | Norman | |
| 6,106,525 A | 8/2000 | Sachse | |
| 6,129,727 A | 10/2000 | Austin | |
| 6,245,071 B1 | 6/2001 | Pierson | |
| 6,277,118 B1 | 8/2001 | Grant | |
| 6,328,737 B1 | 12/2001 | Moorcroft | |
| 6,340,361 B1 | 1/2002 | Kraus | |
| 6,342,054 B1 | 1/2002 | Mata | |
| 6,355,037 B1 | 3/2002 | Crosslin | |
| 6,500,177 B1 | 12/2002 | Martinelli | |
| 6,537,274 B1 | 3/2003 | Katz | |
| 6,537,275 B2 | 3/2003 | Venturini | |
| 6,616,664 B2 | 9/2003 | Walulik | |
| 6,652,524 B1 | 11/2003 | Weiner | |
| 6,689,140 B2 | 2/2004 | Cohen | |
| 6,701,174 B1 | 3/2004 | Krause | |
| 6,702,814 B2 | 3/2004 | Walulik | |
| 6,716,212 B1 | 4/2004 | Pickens | |
| 6,736,775 B2 | 5/2004 | Phillips | |
| 6,746,448 B2 | 6/2004 | Weiner | |
| 6,793,655 B2 | 9/2004 | Orsak | |
| 6,860,883 B2 | 3/2005 | Janowski | |
| 6,964,663 B2 | 11/2005 | Grant | |
| 7,048,735 B2 | 5/2006 | Ferrante | |
| 7,094,240 B2 | 8/2006 | Molz, IV | |
| 7,144,378 B2 | 12/2006 | Arnott | |
| 7,147,640 B2 | 12/2006 | Huebner | |
| 7,226,449 B2 | 6/2007 | Venturini | |
| 7,241,074 B2 | 7/2007 | Thomke | |
| 7,261,713 B2 | 8/2007 | Langmaid | |
| 7,282,052 B2 | 10/2007 | Mullaney | |
| 7,291,148 B2 | 11/2007 | Agee | |
| 7,306,601 B2 | 12/2007 | McGrath | |
| 7,311,711 B2 | 12/2007 | Cole | |
| 7,361,176 B2 | 4/2008 | Cooper | |
| 7,388,972 B2 | 6/2008 | Kitson | |
| 7,422,593 B2 | 9/2008 | Cresina | |
| 7,449,023 B2 | 11/2008 | Walulik | |
| 7,468,063 B2 | 12/2008 | Walulik | |
| 7,479,142 B2 | 1/2009 | Weiner | |
| 7,491,008 B2 | 2/2009 | Thomke | |
| 7,575,575 B2 | 8/2009 | Olsen | |
| 7,578,822 B2 | 8/2009 | Rezach | |
| RE40,914 E | 9/2009 | Taylor | |
| 7,608,074 B2 | 10/2009 | Austin | |
| 7,632,271 B2 | 12/2009 | Baumgartner | |
| 7,645,279 B1 | 1/2010 | Haupt | |
| 7,699,848 B2 | 4/2010 | Hoffman | |
| 7,708,736 B2 | 5/2010 | Mullaney | |
| 7,708,737 B2 | 5/2010 | Kraft | |
| 7,722,651 B2 | 5/2010 | Kwak | |

(56) References Cited

U.S. PATENT DOCUMENTS

| | | |
|---|---|---|
| 7,749,224 B2 | 7/2010 | Cresina |
| 7,763,020 B2 | 7/2010 | Draper |
| 7,769,488 B2 | 8/2010 | Curtis |
| 7,776,046 B2 | 8/2010 | Boyd |
| 7,806,843 B2 | 10/2010 | Marin |
| 7,815,586 B2 | 10/2010 | Grant |
| 7,875,030 B2 | 1/2011 | Hoffmann-Clair |
| 7,881,771 B2 | 2/2011 | Koo |
| 7,887,498 B2 | 2/2011 | Marin |
| 7,931,650 B2 | 4/2011 | Winquist |
| 7,935,115 B2 | 5/2011 | Hagert |
| 7,938,829 B2 | 5/2011 | Mullaney |
| 7,955,333 B2 | 6/2011 | Yeager |
| 7,955,334 B2 | 6/2011 | Steiner |
| 7,985,221 B2 | 7/2011 | Coull |
| 8,002,773 B2 | 8/2011 | Kehres |
| 8,020,753 B2 | 9/2011 | Wheeler |
| 8,029,505 B2 | 10/2011 | Hearn |
| 8,055,487 B2 | 11/2011 | James |
| 8,057,474 B2 | 11/2011 | Knuchel |
| 8,062,293 B2 | 11/2011 | Steiner |
| 8,096,998 B2 | 1/2012 | Cresina |
| 8,114,077 B2 | 2/2012 | Steiner |
| 8,123,747 B2 | 2/2012 | Hajianpour |
| 8,137,347 B2 | 3/2012 | Weiner |
| 8,142,432 B2 | 3/2012 | Matityahu |
| 8,147,490 B2 | 4/2012 | Bauer |
| 8,147,491 B2 | 4/2012 | Lavi |
| 8,157,800 B2 | 4/2012 | Vvedensky |
| 8,167,880 B2 | 5/2012 | Vasta |
| 8,170,719 B2 | 5/2012 | Tsusaka |
| 8,172,849 B2 | 5/2012 | Noon |
| 8,175,749 B2 | 5/2012 | Tsusaka |
| 8,182,483 B2 | 5/2012 | Bagnasco |
| 8,187,274 B2 | 5/2012 | Schulze |
| 8,192,434 B2 | 6/2012 | Huebner |
| 8,202,273 B2 | 6/2012 | Karidis |
| 8,251,937 B2 | 8/2012 | Marin |
| 8,257,353 B2 | 9/2012 | Wong |
| 8,282,652 B2 | 10/2012 | Mackenzi |
| 8,323,282 B2 | 12/2012 | Taylor |
| 8,333,766 B2 | 12/2012 | Edelhauser |
| 8,377,060 B2 | 2/2013 | Vasta |
| 8,388,619 B2 | 3/2013 | Mullaney |
| 8,388,625 B2 | 3/2013 | Bagnasco |
| 8,419,732 B2 | 4/2013 | Mullaney |
| 8,419,750 B2 | 4/2013 | Kienzle, III |
| 8,425,512 B2 | 4/2013 | Vasta |
| 8,425,519 B2 | 4/2013 | Mast |
| 8,425,521 B2 | 4/2013 | Cremer |
| 8,430,878 B2 | 4/2013 | Vasta |
| 8,439,914 B2 | 5/2013 | Ross |
| 8,444,644 B2 | 5/2013 | Ross |
| 8,454,604 B2 | 6/2013 | Wong |
| 8,469,958 B2 | 6/2013 | Stevens |
| 8,469,966 B2 | 6/2013 | Allen |
| 8,506,566 B2 * | 8/2013 | Karidis .................. A61B 17/66 606/57 |
| 8,523,858 B2 | 9/2013 | Lessig |
| 8,574,232 B1 | 11/2013 | Ross |
| 8,608,740 B2 | 12/2013 | Buetikofer |
| 8,623,061 B2 | 1/2014 | Quevedo |
| 8,654,150 B2 | 2/2014 | Haskell |
| 8,679,117 B2 | 3/2014 | Knuchel |
| 8,702,705 B2 | 4/2014 | Ziran |
| 8,834,467 B2 | 9/2014 | Singh |
| 8,858,555 B2 | 10/2014 | Crozet |
| 8,864,763 B2 * | 10/2014 | Murray .................. A61B 17/66 606/56 |
| 9,078,700 B2 * | 7/2015 | Ross .................. A61B 17/6475 |
| 9,717,530 B1 * | 8/2017 | Ross .................. A61B 17/645 |
| 2001/0049525 A1 | 12/2001 | Slocum |
| 2001/0049526 A1 | 12/2001 | Venturini |
| 2002/0010465 A1 * | 1/2002 | Koo .................. A61B 17/62 606/57 |
| 2002/0013584 A1 | 1/2002 | Termaten |
| 2002/0042613 A1 | 4/2002 | Mata |
| 2002/0072753 A1 | 6/2002 | Cohen |
| 2002/0165543 A1 | 11/2002 | Winquist |
| 2003/0069580 A1 | 4/2003 | Langmaid |
| 2003/0109879 A1 | 6/2003 | Orsak |
| 2003/0114852 A1 | 6/2003 | Biedermann |
| 2003/0149429 A1 | 8/2003 | Ferrante |
| 2003/0149430 A1 | 8/2003 | Ferrante |
| 2003/0153910 A1 | 8/2003 | Janowski |
| 2003/0181911 A1 | 9/2003 | Venturini |
| 2003/0191466 A1 | 10/2003 | Austin |
| 2003/0216734 A1 | 11/2003 | Mingozzi |
| 2003/0225405 A1 | 12/2003 | Weiner |
| 2003/0225406 A1 | 12/2003 | Weiner |
| 2004/0059331 A1 | 3/2004 | Mullaney |
| 2004/0068187 A1 | 4/2004 | Krause |
| 2004/0073211 A1 | 4/2004 | Austin |
| 2004/0073212 A1 | 4/2004 | Kim |
| 2004/0097922 A1 | 5/2004 | Mullaney |
| 2004/0097944 A1 | 5/2004 | Koman |
| 2004/0116926 A1 | 6/2004 | Venturini |
| 2004/0167518 A1 | 8/2004 | Estrada |
| 2004/0230191 A1 | 11/2004 | Frey |
| 2004/0249375 A1 | 12/2004 | Agee |
| 2005/0015087 A1 | 1/2005 | Walulik |
| 2005/0043730 A1 | 2/2005 | Janowski |
| 2005/0043731 A1 | 2/2005 | Labbe |
| 2005/0059968 A1 | 3/2005 | Grant |
| 2005/0085810 A1 | 4/2005 | Lutz |
| 2005/0113829 A1 | 5/2005 | Walulik |
| 2005/0119656 A1 | 6/2005 | Ferrante |
| 2005/0149018 A1 | 7/2005 | Cooper |
| 2005/0149086 A1 | 7/2005 | Huxel |
| 2005/0165394 A1 | 7/2005 | Boyce |
| 2005/0215997 A1 | 9/2005 | Austin |
| 2005/0261680 A1 | 11/2005 | Draper |
| 2006/0155276 A1 | 7/2006 | Walulik |
| 2006/0184169 A1 | 8/2006 | Stevens |
| 2006/0229602 A1 | 10/2006 | Olsen |
| 2006/0229605 A1 | 10/2006 | Olsen |
| 2006/0276786 A1 | 12/2006 | Brinker |
| 2006/0287652 A1 | 12/2006 | Lessig |
| 2007/0038217 A1 | 2/2007 | Brown |
| 2007/0043354 A1 | 2/2007 | Koo |
| 2007/0049930 A1 | 3/2007 | Hearn |
| 2007/0055234 A1 | 3/2007 | McGrath |
| 2007/0161983 A1 | 7/2007 | Cresina |
| 2007/0161984 A1 | 7/2007 | Cresina |
| 2007/0225704 A1 * | 9/2007 | Ziran .................. A61B 17/66 606/57 |
| 2007/0282338 A1 | 12/2007 | Mullaney |
| 2008/0021451 A1 | 1/2008 | Coull |
| 2008/0051779 A1 | 2/2008 | Mackenzie |
| 2008/0228185 A1 | 9/2008 | Vasta |
| 2008/0234554 A1 | 9/2008 | Vvedensky |
| 2008/0269741 A1 | 10/2008 | Karidis |
| 2008/0281332 A1 | 11/2008 | Taylor |
| 2009/0018541 A1 | 1/2009 | Lavi |
| 2009/0036890 A1 | 2/2009 | Karidis |
| 2009/0036891 A1 | 2/2009 | Brown |
| 2009/0036892 A1 | 2/2009 | Karidis |
| 2009/0082776 A1 | 3/2009 | Cresina |
| 2009/0088751 A1 | 4/2009 | Mullaney |
| 2009/0105621 A1 | 4/2009 | Boyd |
| 2009/0131935 A1 | 5/2009 | Yeager |
| 2009/0177197 A1 | 7/2009 | Marin |
| 2009/0177198 A1 | 7/2009 | Theodoros |
| 2009/0198235 A1 | 8/2009 | Steiner |
| 2009/0264882 A1 | 10/2009 | Steiner |
| 2009/0264883 A1 | 10/2009 | Steiner |
| 2009/0275944 A1 | 11/2009 | Huebner |
| 2009/0287212 A1 | 11/2009 | Hirata |
| 2009/0292285 A1 | 11/2009 | Salzhauer |
| 2009/0312757 A1 | 12/2009 | Kehres |
| 2009/0326532 A1 | 12/2009 | Schulze |
| 2010/0087819 A1 | 4/2010 | Mullaney |
| 2010/0114103 A1 | 5/2010 | Harrison |
| 2010/0125273 A1 | 5/2010 | Schwieger |

(56) References Cited

U.S. PATENT DOCUMENTS

| | | |
|---|---|---|
| 2010/0145336 A1 | 6/2010 | Draper |
| 2010/0179548 A1 | 7/2010 | Marin |
| 2010/0191239 A1 | 7/2010 | Sakkers |
| 2010/0234844 A1 | 9/2010 | Edelhauser |
| 2010/0234845 A1 | 9/2010 | Mullaney |
| 2010/0249779 A1 | 9/2010 | Hotchkiss |
| 2010/0280516 A1 | 11/2010 | Taylor |
| 2010/0286826 A1 | 11/2010 | Tsusaka |
| 2010/0298827 A1 | 11/2010 | Cremer |
| 2010/0305568 A1 | 12/2010 | Ross |
| 2010/0312243 A1 | 12/2010 | Ross |
| 2010/0318084 A1 | 12/2010 | Hajianpour |
| 2010/0331840 A1 | 12/2010 | Ross |
| 2011/0004199 A1 | 1/2011 | Ross |
| 2011/0060336 A1 | 3/2011 | Pool |
| 2011/0066151 A1 | 3/2011 | Muerner |
| 2011/0082458 A1 | 4/2011 | Crozet |
| 2011/0103676 A1 | 5/2011 | Mullaney |
| 2011/0118737 A1 | 5/2011 | Vasta |
| 2011/0118738 A1* | 5/2011 | Vasta .................. A61B 17/62 606/56 |
| 2011/0125196 A1 | 5/2011 | Quevedo |
| 2011/0172663 A1 | 7/2011 | Mullaney |
| 2011/0172664 A1 | 7/2011 | Bagnasco |
| 2011/0178638 A1 | 7/2011 | Tsusaka |
| 2011/0196380 A1 | 8/2011 | Cremer |
| 2011/0208186 A1 | 8/2011 | Marin |
| 2011/0208187 A1* | 8/2011 | Wong .................. A61B 17/6416 606/56 |
| 2011/0245830 A1 | 10/2011 | Zgonis |
| 2011/0288549 A1 | 11/2011 | Steiner |
| 2011/0313418 A1 | 12/2011 | Nikonovas |
| 2011/0313419 A1 | 12/2011 | Mullaney |
| 2012/0004659 A1 | 1/2012 | Miller |
| 2012/0029516 A1 | 2/2012 | Taylor |
| 2012/0041439 A1 | 2/2012 | Singh |
| 2012/0078251 A1 | 3/2012 | Benenati |
| 2012/0089142 A1 | 4/2012 | Mullaney |
| 2012/0095462 A1 | 4/2012 | Miller |
| 2012/0136355 A1 | 5/2012 | Wolfson |
| 2012/0143190 A1 | 6/2012 | Wolfson |
| 2012/0184958 A1 | 7/2012 | Knuchel |
| 2012/0215222 A1 | 8/2012 | Yapp |
| 2012/0232554 A1 | 9/2012 | Shaevitz |
| 2012/0277744 A1 | 11/2012 | Lindahl |
| 2012/0303028 A1 | 11/2012 | Wong |
| 2012/0303029 A1* | 11/2012 | Vasta .................. A61B 17/60 606/56 |
| 2013/0123784 A1 | 5/2013 | Ross |
| 2013/0131675 A1 | 5/2013 | Vasta |
| 2013/0131676 A1 | 5/2013 | Mullaney |
| 2013/0245625 A1 | 9/2013 | Vasta |
| 2013/0253511 A1 | 9/2013 | Cheng |
| 2013/0253513 A1 | 9/2013 | Ross |
| 2013/0289575 A1 | 10/2013 | Edelhauser |
| 2013/0310880 A1 | 11/2013 | Ruiz |
| 2014/0046326 A1 | 2/2014 | Wong |
| 2014/0058389 A1* | 2/2014 | Singh .................. A61B 17/62 606/56 |
| 2014/0066931 A1 | 3/2014 | Myers |
| 2014/0094857 A1 | 4/2014 | Quevedo |
| 2014/0128868 A1 | 5/2014 | Harrison |

FOREIGN PATENT DOCUMENTS

| | | |
|---|---|---|
| DE | 3802743 A1 | 8/1989 |
| DE | 3935134 A1 | 4/1991 |
| DE | 102005013617 A1 | 9/2006 |
| EP | 0140786 A2 | 5/1985 |
| EP | 0420430 A1 | 4/1991 |
| EP | 0512792 A1 | 11/1992 |
| EP | 0522242 A1 | 1/1993 |
| EP | 611007 A1 | 8/1994 |
| WO | 8503449 A1 | 8/1985 |
| WO | 8911255 A1 | 11/1989 |
| WO | 9106253 A1 | 5/1991 |
| WO | 9111151 A1 | 8/1991 |
| WO | 9207526 A1 | 5/1992 |
| WO | 9418898 A1 | 9/1994 |
| WO | 1997030650 A1 | 8/1997 |
| WO | 2006100283 A1 | 9/2006 |
| WO | 2015065306 A1 | 5/2015 |
| WO | 2015136544 A1 | 9/2015 |

* cited by examiner

GEAR MECHANISMS FOR FIXATION FRAME STRUTS

CROSS-REFERENCE TO RELATED APPLICATIONS

The present application is a continuation of U.S. patent application Ser. No. 17/006,979, filed Aug. 31, 2020, which is a continuation of U.S. patent application Ser. No. 15/948,219, filed Apr. 9, 2018, which is a continuation of U.S. Pat. No. 10,010,350, filed Jun. 14, 2016, the disclosures of which are hereby incorporated by reference herein.

BACKGROUND OF THE DISCLOSURE

The present disclosure relates to systems and components of external fixation frames. More particularly, the present disclosure relates to struts and strut components using gear mechanisms for manipulation of an external fixation frame.

Many different types of bone deformities can be corrected using external fixation systems to perform the distraction osteogenesis process. For example, an Ilizarov device or similar external fixation system may be used. Such systems generally use rings also designated as fixation plates connected by threaded rods or struts for manipulation, lengthening, angulation, rotation, and translation of deformities of bones.

As the struts are manipulated, the rings or fixation plates change positions relative to one another, causing the bones or bone segments attached to the fixation plates to change positions relative to one another, until the bone segments are in a desired position relative to one another. Fixation systems have many areas which may be improved including, for example, the ease and precision with which the fixation system may be adjusted by a user, whether a clinician or a patient.

BRIEF SUMMARY

According to a first aspect of the disclosure, an adjustable length strut includes a first joint member proximate a first end of the strut, a second joint member proximate a second end of the strut opposite the first end, and a rod member extending between the first joint member and the second joint member, the rod member including external threads. A tube member extends between the first joint member and the second joint member, the tube member including a hollow portion adapted to receive the rod member and an engagement feature adapted to engage the external threads of the rod member. An actuation mechanism is rotatably fixed to the rod member, the actuation mechanism including a plurality of gear teeth extending radially outward of a longitudinal axis of the rod member. A protrusion member may be coupled to an end portion of the rod member, the protrusion member extending substantially orthogonal to the longitudinal axis of the rod member. The protrusion member may include a collar portion substantially surrounding the end portion of the rod member, and the collar portion may be freely rotatable with respect to the end portion of the rod member. The tube member may include an elongate slot extending through inner and outer surfaces of the tube member. A portion of the protrusion member may extend through a portion of the elongate slot. The tube member may include visual indicia on the outer surface thereof adjacent the slot.

According to another aspect of the disclosure, an external fixation frame system includes a first support ring having a plurality of first apertures extending therethrough, a second support ring having a plurality of second apertures extending therethrough, and at least one telescopic strut. The telescopic strut includes a first joint member proximate a first end of the strut, the first joint member adapted to be coupled to the first support ring, and a second joint member proximate a second end of the strut opposite the first end, the second joint member adapted to be coupled to the second support ring. The telescopic strut also includes a rod member extending between the first joint member and the second joint member, the rod member including external threads. A tube member extends between the first joint member and the second joint member, the tube member including a hollow portion adapted to receive the rod member and an engagement feature adapted to engage the external threads of the rod member. An actuation mechanism is rotatably fixed to the rod member, the actuation mechanism including a plurality of gear teeth extending radially outward of a longitudinal axis of the rod member. The first joint member may include a first borehole extending along the longitudinal axis of the rod member. A first fastener may be adapted to extend through one of the first apertures in the first support ring and into the first borehole of the first joint member to rotatably fix the first joint member about the longitudinal axis of the rod member. The first joint member may include a second borehole extending substantially orthogonally to the first borehole, the second borehole adapted to receive a tool therein to prevent rotation of the first joint member about the longitudinal axis of the rod member as the first fastener is coupled within the first borehole. The second joint member may include a third borehole extending along the longitudinal axis of the rod member. A second fastener may be adapted to extend through one of the second apertures in the second support ring and into the third borehole of the second joint member to rotatably fix the second joint member and the tube member about the longitudinal axis of the rod member. The second joint member may include a fourth borehole extending substantially orthogonally to the third borehole, the fourth borehole adapted to receive a tool therein to prevent rotation of the second joint member and the tube member about the longitudinal axis of the rod member as the second fastener is coupled within the third borehole.

The external fixation frame system may also include a modular attachment member adapted to be coupled to the first joint, the modular attachment member including a worm gear adapted to engage the gear teeth of the actuation mechanism. The modular attachment member may include a bolt extending at least partially within the worm gear, the bolt being rotatably fixed with respect to the worm gear. A radiofrequency identification tag member may be positioned at least partially within the modular attachment member. The bolt may be adapted to extend along an axis substantially orthogonal to a longitudinal axis of the rod member when the modular attachment piece is coupled to the strut. The bolt may include visual indicia and the strut may include an indicator member coupled to the strut, the indicator member and the visual indicia each having a corresponding marking. The first joint member may be coupled to the first support ring by a first offset plate so that the first joint member is positioned radially outward of the first support ring and the second joint member is coupled to the second support ring by a second offset plate so that the second joint member is positioned radially outward of the second support ring.

DETAILED DESCRIPTION

Figure 1:
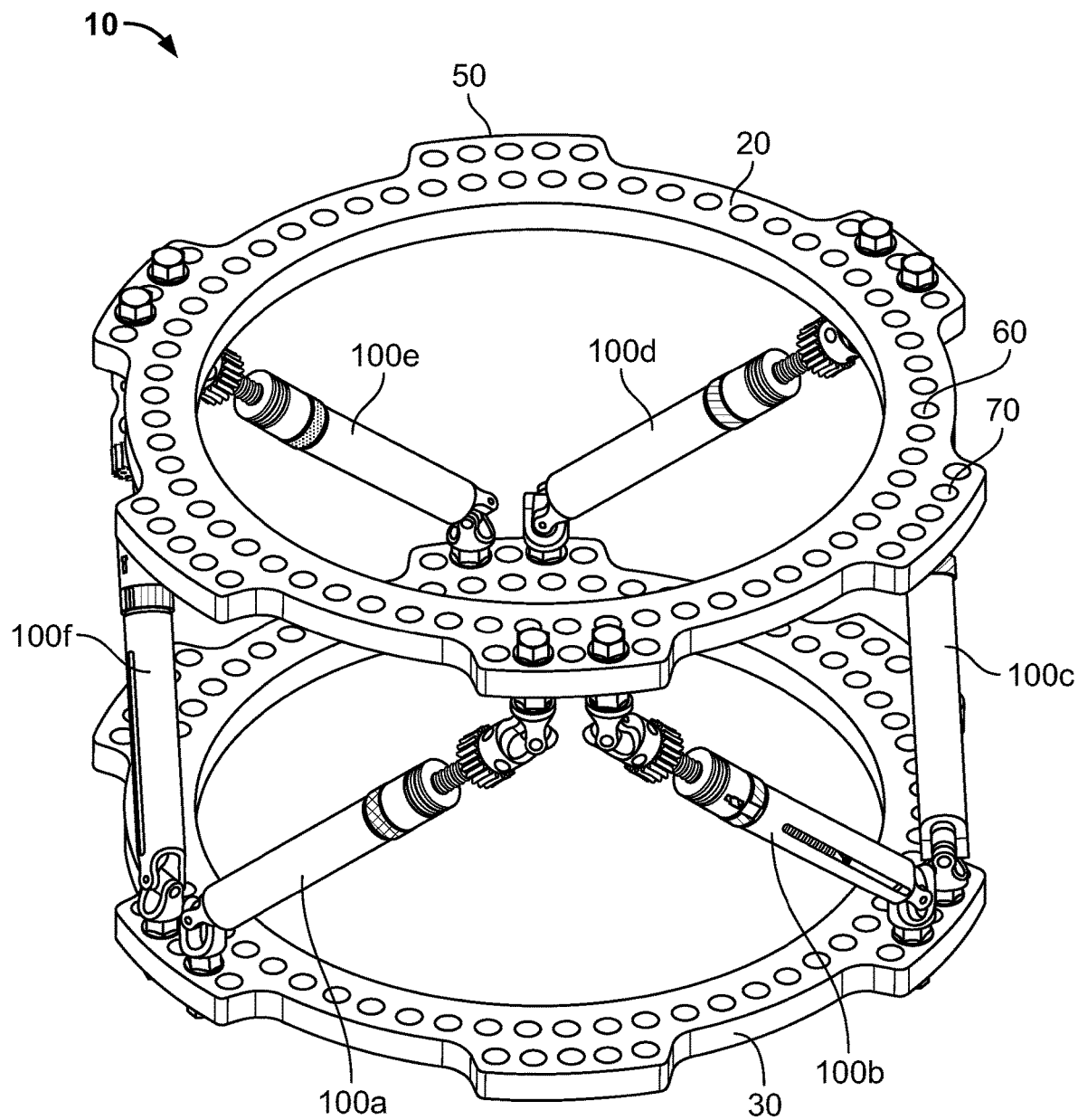
FIG. 1 is a perspective view of an external fixation system according to an embodiment of the disclosure.

FIG. 1 shows an external fixation frame 10 in an assembled condition according to one aspect of the disclosure. Generally, fixation frame 10 includes a first ring 20 and a second ring 30, with six telescopic struts 100a-f coupling the first ring 20 to the second ring 30. The first ring 20 may also be referred to as a proximal ring or a reference ring, while the second ring 30 may also be referred to as a distal ring or a moving ring. In the illustrated embodiment, each strut 100a-f includes a threaded portion that may thread into or out of a tube portion, for example by interaction with quick release mechanism 130, to decrease or increase the length, respectively, of the telescopic strut. Each end of each strut 100a-f may be coupled to the first ring 20 and second ring 30 via a joint mechanism, such as a ball joint, a constrained hinge joint, or a universal joint as illustrated. The use of universal joints on each end of the strut provides for six degrees of freedom of motion of the external fixation system 10. It should be understood that although the disclosure is generally described in the context of closed circular rings, the concepts described herein may apply with equal force to other types of rings, such as open rings and/or U-shaped rings.

In external fixation system 10, telescopic struts 100a-f are used to reduce fractures and correct deformities over time. Patients correct the deformities by prescribed adjustments of the struts 100a-f. The lengths of the struts 100a-f are adjusted over time to change the position and orientation of the two rings 20, 30 with respect to one another, which in turn repositions and reorients the bone fragments, with a goal of correcting the bone deformity. The adjustment of the external fixator 10 should strictly comply with the predetermined correction plan.

Rings 20 and 30 of external fixation system 10 may include a plurality of extension tabs 50. In the illustrated example, each ring 20 and 30 includes six extension tabs 50 spaced circumferentially around the perimeter of the respective rings, although more or fewer may be suitable depending on the particular components of the fixation system. In addition to what is described directly below, extension tabs 50 may help increase the cross-sectional area of rings 20, 30 and thus provide for increased stiffness of the rings.

With this configuration, each ring 20, 30 includes a first inner circumferential row of holes 60 and a second outer circumferential row of holes 70. As illustrated, the second outer circumferential row of holes 70 may be only positioned on the plurality of extension tabs 50 on the rings 20 and 30. It should be understood that although the second outer circumferential row of holes 70 is shown in FIG. 1 as being positioned solely on extension tabs 50, top ring 20 and/or bottom ring 30 may contain two complete rows of holes, for example with a completely circular (or nearly completely circular) geometry. The use of extension tabs 50, compared to two full circumferential rows of holes, may help reduce overall bulk of rings 20, 30 and also provide for intuitive strut placement for surgical personnel. The completely circular version of rings 20, 30 with two full (or nearly full) rows of circumferential holes may be particularly suited for relatively small diameter rings, although indentations or other features may be introduced to provide an intuitive interface for strut placement by surgical personnel. Further, in the illustrated embodiment, the first and second circumferential rows of holes 60 and 70 are positioned so that the first row of holes 60 does not align radially with the second row of holes 70. In other words, the first row of holes 60 has a staggered configuration with respect to the second row of holes 70. The additional hole options may also be utilized for connecting other components, such as fixation pins to couple the rings 20, 30 to the respective bone fragments. Still further, the staggered configuration of holes between the first and second rows 60, 70 may also help prevent interference between components attached to nearby holes, for example such as a strut 100a-f positioned in a first hole and a fixation pin or other fixation member attached to an adjacent or nearby second hole. For example, a relatively thin wire extending radially from one of the holes in the first circumferential row 60 may not radially interfere with a hole positioned in the second circumferential row 70 because of the radial staggering. It should be understood that the size of the tabs 50 may increase or decrease depending on the diameter of the rings 20 and 30, with greater diameter rings 20 and 30 having larger tabs 50 with more holes 70 compared to smaller diameter rings. For example, the illustrated tabs 50 include six holes 70, and a smaller ring may include smaller tabs with four holes each, for example.

Figure 2A:
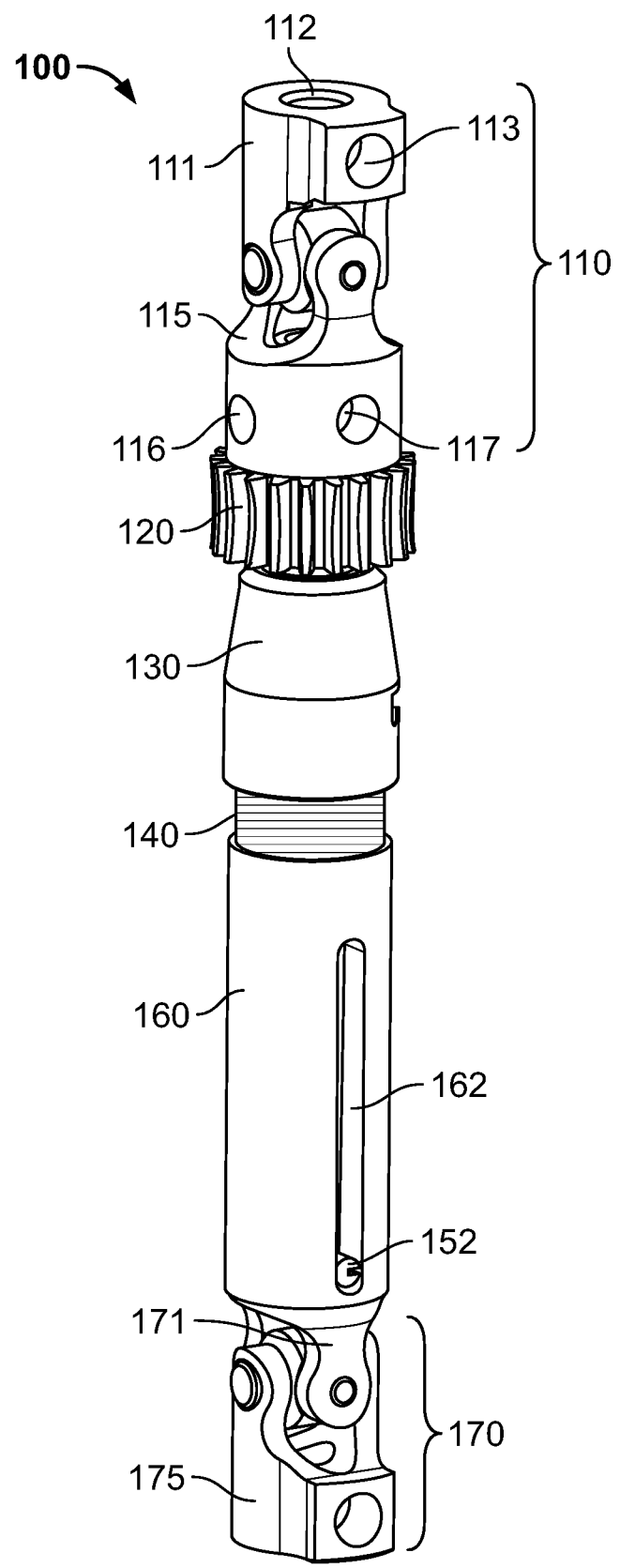
FIG. 2A is a perspective view of a strut of the external fixation system of FIG. 1.

FIG. 2A illustrates a perspective view of one telescopic strut 100 from the external fixation system 10 of FIG. 1. It should be understood that the components of struts 100a-f may be identical to one another, although some struts 100a-f may have different sizes than other struts 100a-f and may include different indicia, such as colors or markings for identification purposes, as described in greater detail below. For purposes of this disclosure, the term proximal refers to the top of the strut 100 in the orientation of FIG. 2A, and the term distal refers to the bottom of the strut 100 in the orientation of FIG. 2A. The proximal end portion of strut 100 may include a first joint 110, which is shown in this example as a universal joint. Joint 110 may include a proximal portion 111, which may include a first aperture 112 aligned substantially parallel with the longitudinal axis of strut 100 and a second aperture 113 aligned substantially transverse or orthogonal to the first aperture 112. The first aperture 112 may be configured to receive a fastener that passes through a hole in proximal ring 20 to secure the proximal portion 111 of joint 110 to proximal ring 20. The fastener may be connected so that the proximal portion 111 does not rotate relative to proximal ring 20. The second aperture 113 may be configured to receive a portion of a tool to prevent proximal portion 111 from rotating, for example while a fastener is being screwed into or otherwise inserted into first aperture 112. Joint 110 may also include a distal portion 115 with a first aperture 116 and a second aperture 117, the first and second apertures 116, 117 being aligned substantially transverse and/or orthogonal to one another and to the longitudinal axis of strut 100. First and second apertures 116, 117 may be used as attachment points for attaching additional components to strut 100, which is explained in greater detail below in connection with FIGS. 4A-C.

Still referring to FIG. 2A, strut 100 may include additional components including an actuation mechanism 120, a quick-release mechanism 130, a strut identifier 140, a threaded rod 150 (not visible in FIG. 2A), a tube 160, and a second joint 170. As noted above, the effective length of strut 100, which may be thought of as the distance between the proximal end and distal end of strut 100, may be adjusted by threading the threaded rod 150 of strut 100 into or out of tube 160 through interaction with quick-release mechanism 130.

Figure 2B:
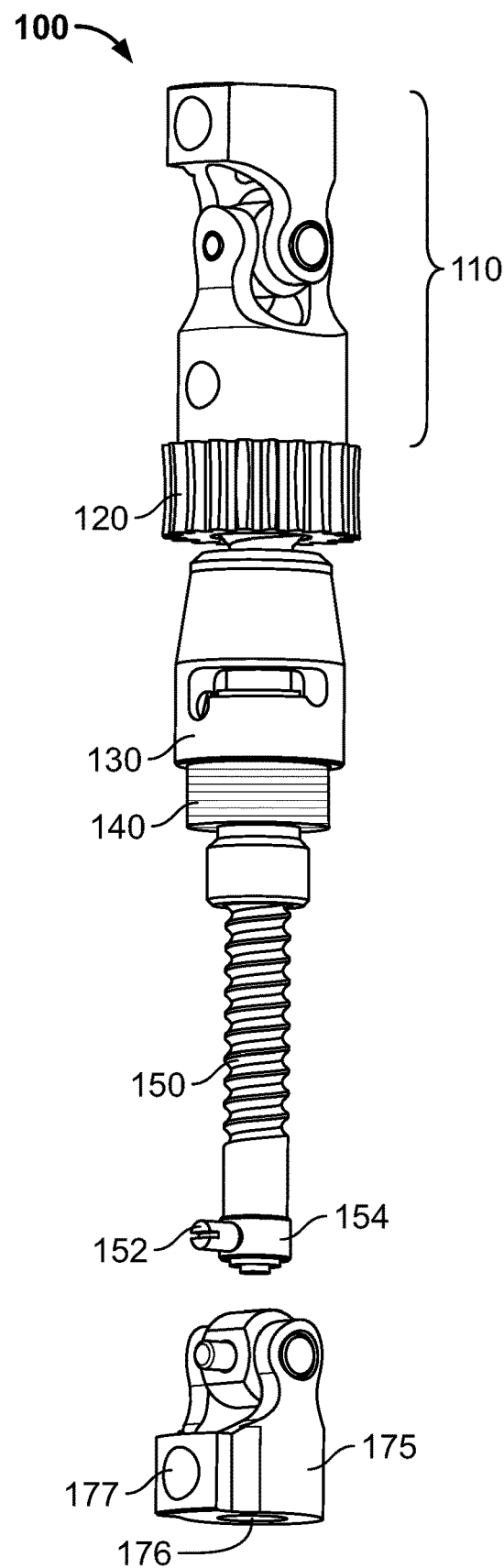
FIGS. 2B-C are a perspective views of the strut of FIG. 2A with certain components omitted.
Figure 2C:
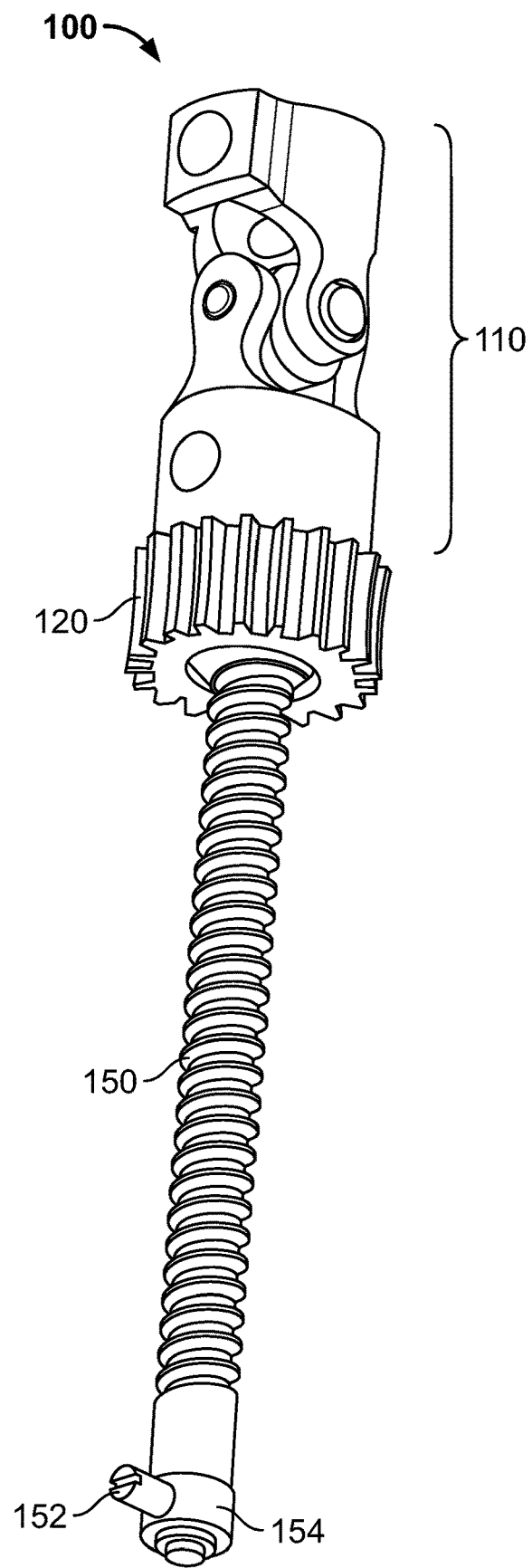

FIG. 2B illustrates strut 100 with tube 160 omitted for clarify of illustration. FIG. 2C illustrates strut 100 with tube 160, as well as quick-release mechanism 130, strut identified 140, and second joint 170 omitted for clarity of illustration.

Figure 2D:
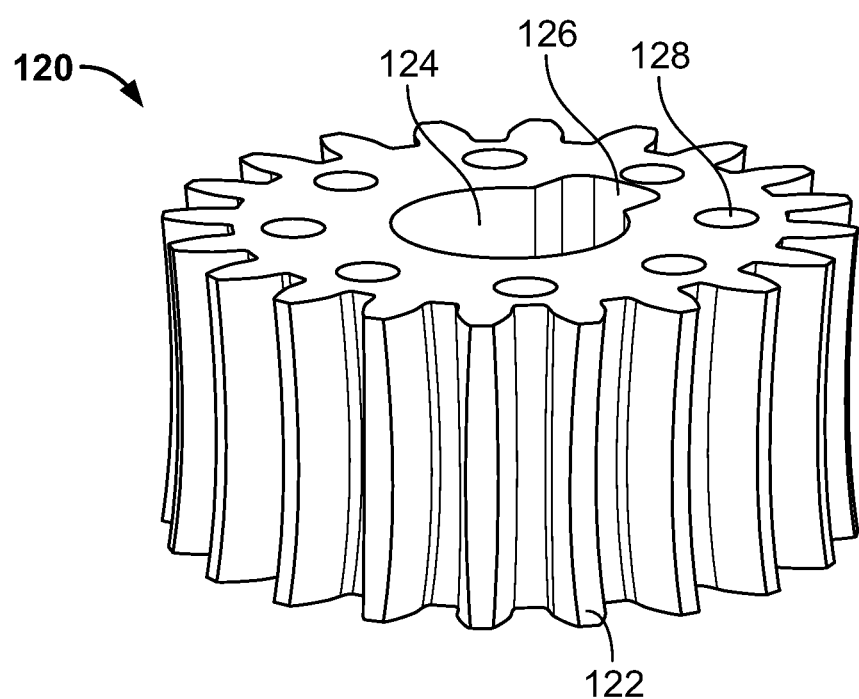
FIG. 2D is a perspective view of an actuation mechanism of the strut of FIG. 2A.

Actuation mechanism 120 is shown isolated in FIG. 2D. Actuation mechanism 120 may be generally a short, cylindrical component with a plurality of ridges or gear teeth 122 extending around the circumference of actuation mechanism 120. The actuation mechanism 120 may be rotatably coupled to threaded rod 150 so that rotation of actuation mechanism 120 causes a corresponding rotation of threaded rod 150. For example, actuation mechanism 120 may have a channel 124 extending therethrough, with an extension 126 in channel 124 that mates with a corresponding extension in threaded rod 150, so that rotation of actuation mechanism 120 causes rotation of threaded rod 150. It should be understood that the threaded rod 150 may rotate with respect to the first joint 110, the first joint 110 and second joint 170 being rotatably fixed to rings 20 and 30, respectively. The proximal surface of actuation mechanism may include a plurality of divots of grooves 128 sized to accept a ball which is biased into the groove via a spring. The spring may have a first end in contact with a distal surface of first joint 110, with a distal end pressing a ball into the proximal surface of actuation mechanism 120. With this configuration, an amount of force is required to rotate actuation mechanism 120 to overcome the force of the spring pushing the ball into the divot 128. As rotation of actuation mechanism 120 continues, the ball will eventually be positioned adjacent an adjacent groove 128. As rotation continues further, the spring will force the ball into the next groove 128 when the ball is aligned with the groove 128, causing a tactile and/or audible click. Each "click" may correspond to a particular axial change in length so that a user knows, for example, that four "clicks" correspond to 1 mm of length adjustment. Similar "clicking mechanisms" are described in greater detail in U.S. Pat. No. 8,834,467, the contents of which are hereby incorporated by reference herein.

Referring now to FIGS. 2A-B, quick-release mechanism 130 may generally take the form of an outer housing that surrounds a portion of threaded rod 150. Quick-release mechanism 130 may have a disengaged state and an engaged state. In the disengaged state, threaded rod 150 may be capable of moving into or out of tube 160 without rotation of the threaded rod 150, for quick adjustments of the length of strut 100, which may be useful for example while initially assembling the fixation frame 10. Rotating the quick-release mechanism 130 may transition the quick-release mechanism 130 into the engaged state, in which threated rod 150 may only move axially into or out of tube 160 via rotation of the threaded rod 150. The mechanism for keeping the quick-release mechanism 130 in the engaged state may include a ball or other feature that is forced between adjacent threads of threaded rod 150 so that axial translation of the threaded rod 150 is only possible via rotation, so that rotation of threaded rod 150 axially moves the threaded rod 150 into the tube 160, without requiring the tube 160 to have internal threading. It should be understood that the quick-release mechanism 130 is not a necessary component of strut 100, and may be omitted from strut 100 if desired. If quick-release mechanism 130 is omitted, it may be preferably to include internal threads on tube 160 to correspond to external threads on threaded rod 150. Further details of quick-release mechanisms have been described elsewhere, including, for example, in U.S. Pat. No. 9,101,398, the contents of which are hereby incorporated by reference herein.

A strut identifier 140 may be coupled to strut 100 at any desired location, for example between the quick-release mechanism 130 and the tube 160. Strut identifier 140 may take the form of a clip or any other suitable shape that can be quickly and securely clipped onto the strut 100 and removed from strut 100. For example, in the illustrated embodiment, strut identifier 140 is a "C"-shaped clip that is flexible enough to open for easy connection to strut 100, but rigid enough that the strut identifier 140 is not easily removed from strut 100 without intentional application of force. Strut identifier 140 may have a color or other identifier such as a number, letter, or shape pattern. Each strut 100a-f may have a strut identifier 140 that is structurally similar or identical, but that each has easily distinguishable indicia, such as different colors, different numbers, etc. Strut identifiers 140 may be used so that each strut 100a-f is easily distinguished from one another, and so that other matching indicia may be provided on other components, described in greater detail below, that may be added onto struts 100a-f so that each additional component may be easily matched with the correct corresponding strut 100a-f. Strut identifier 140 may also function to prevent unintentional disengagement of the quick release mechanism 130.

Referring again to FIG. 2A, tube 160 may be a generally hollow cylindrical tube configured to allow threaded rod 150 to move axially into or out of tube 160 to decrease or increase the effective length of strut 100, respectively. As noted above, such axial movement may be produced by rotation of threaded rod 150 when the quick release mechanism 130 is in the engaged position, so that the threads of the threaded rod 150 engage the ball or other mechanism within the quick release mechanism 130. If omitting the quick release mechanism 130, the tube 160 may include internal threads that mate directly with the external threads of the threaded rod 150. A slot 162 may extend along part of the length of the tube 160, the slot 162 opening the hollow inside of the tube 160 to the exterior of the tube. The slot 162 may have a width slightly larger than the width of button 152. Referring now to FIGS. 2B-C, the distal end of threaded rod 150 may include a button 152 coupled to a collar 154, the collar 154 surrounding the distal end of threaded rod 150. Collar 154 may be positioned with a groove at the distal end of threaded rod 150 so that collar 154 may rotate freely around the axis of the strut 100 while being axially fixed with respect to the threaded of 150. Referring again to FIG. 2A, as threaded rod 150 is threaded into or out of tube 160, button 152 travels up or down the slot 162 of the tube 160, which is possible because button 152 and collar 154 are free to rotate with respect to threaded rod 150. Tube 160 may include indicia, such as hash marks and/or measurements, on or adjacent to slot 162. The position of button 152 along slot 162 may correspond to the effective length of the strut 100, so that a user can easily determine the effective length of the strut based on the indicia adjacent to the position of button 152 at any particular time.

Referring still to FIG. 2A, the distal end of tube 160 may include two extensions that form a proximal portion 171 of second joint 170. Second joint 170 may include a distal portion 175 that, together with proximal portion 171 and an internal mechanism form a universal joint similar to first joint 110. Distal portion 175 may include a first aperture 176 that is aligned substantially parallel with strut 100. Aperture 176 may be adapted to receive a fastener therein to couple second joint 170 to distal ring 30. The fastener may be a screw or other type of fastener, and may be adapted to tightly couple the second joint 170 to the distal ring 30 so that the second joint 170 does not rotate with respect to distal ring 30. With this configuration, the slot 162 of tube 160 may be positioned outward (away from the center of proximal and distal rings 20, 30) so that the position of button 152 with respect to indicia on tube 160 may be easily read at all times. The distal portion 175 of second joint 170 may include a second aperture 177 aligned substantially orthogonal to first aperture 176 and adapted to receive a tool to keep second joint 170 from rotating, for example while a fastener is screwed into first aperture 176. This may help ensure, for example, the slot 162 of tube 160 is facing away from the center of the rings 20, 30 as the strut 100 is tightened to the rings 20, 30. It should also be understood that in some prior art devices, rotational freedom of the strut was provided by loosely coupling the joint(s) to the ring(s) so that the joints themselves could swivel. In the present disclosure, the rotational degree of freedom is provided by the ability of threaded rod 150 to rotate, while the tight attachment of the first joint 110 and second joint 170 to the first ring 20 and second ring 30 provides for a more stable connection.

Figure 3:
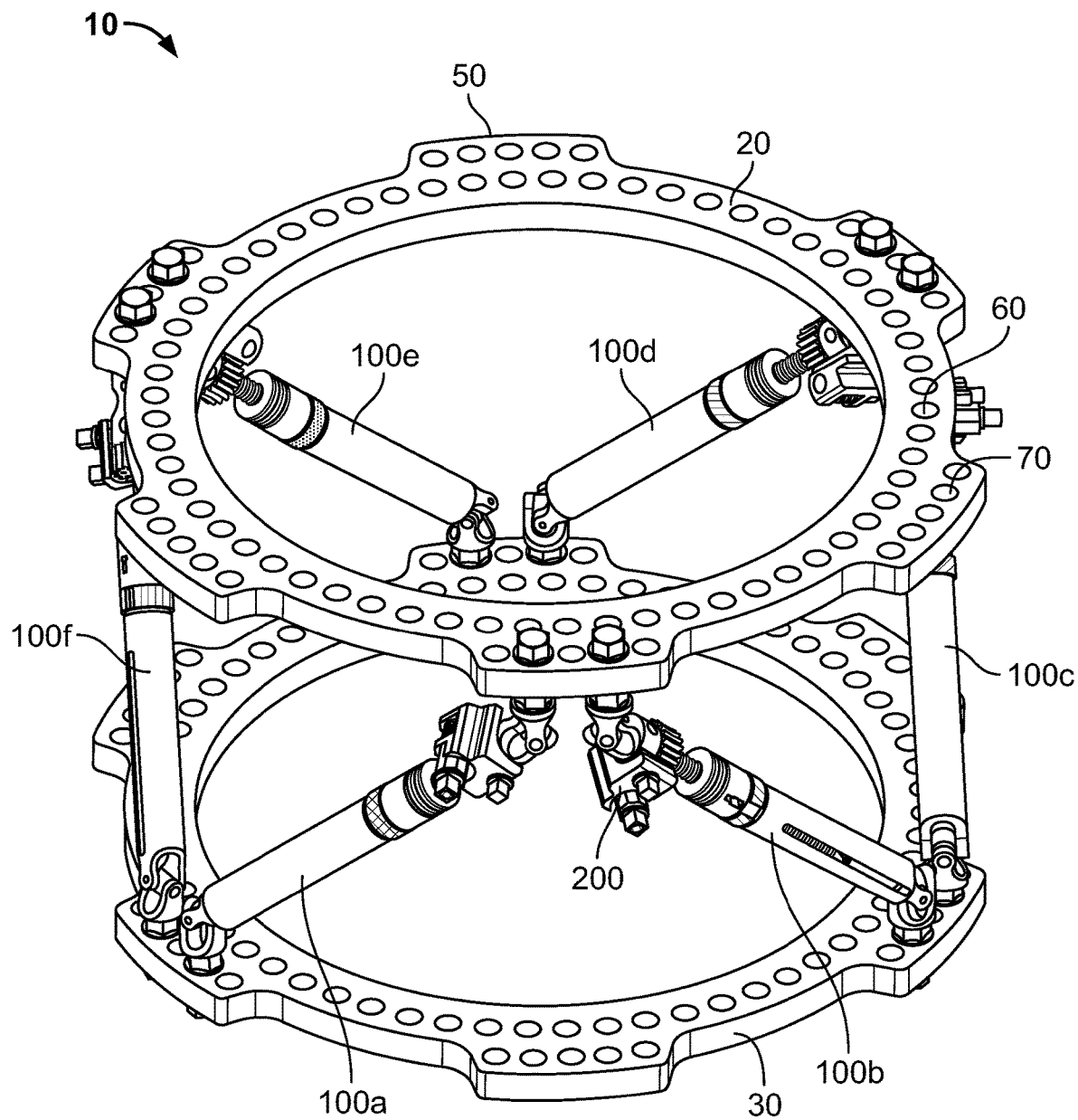
FIG. 3 is a perspective view of the external fixation system of FIG. 1 with modular attachment members coupled to the struts.

It should be understood that strut 100 as described above may be designed for manual actuation, for example by a user gripping the actuation mechanism 120 with his hand and manually rotating the actuation mechanism 120. However, it should be understood that a tool may be used, either directly on actuation mechanism 120 or with intervening components, to adjust the length of strut 100. For example, FIG. 3 illustrates the external fixation system 10 of FIG. 1 with completely identical components, with the exception that each strut 100a-f includes a modular attachment piece 200 coupled to a corresponding strut 100a-f. As is described in greater detail below, modular attachment piece 200 provides a variety of benefits, including a simple way to allow a user to adjust struts 100a-f with a tool rather than through manual adjustment.

Figure 4A:
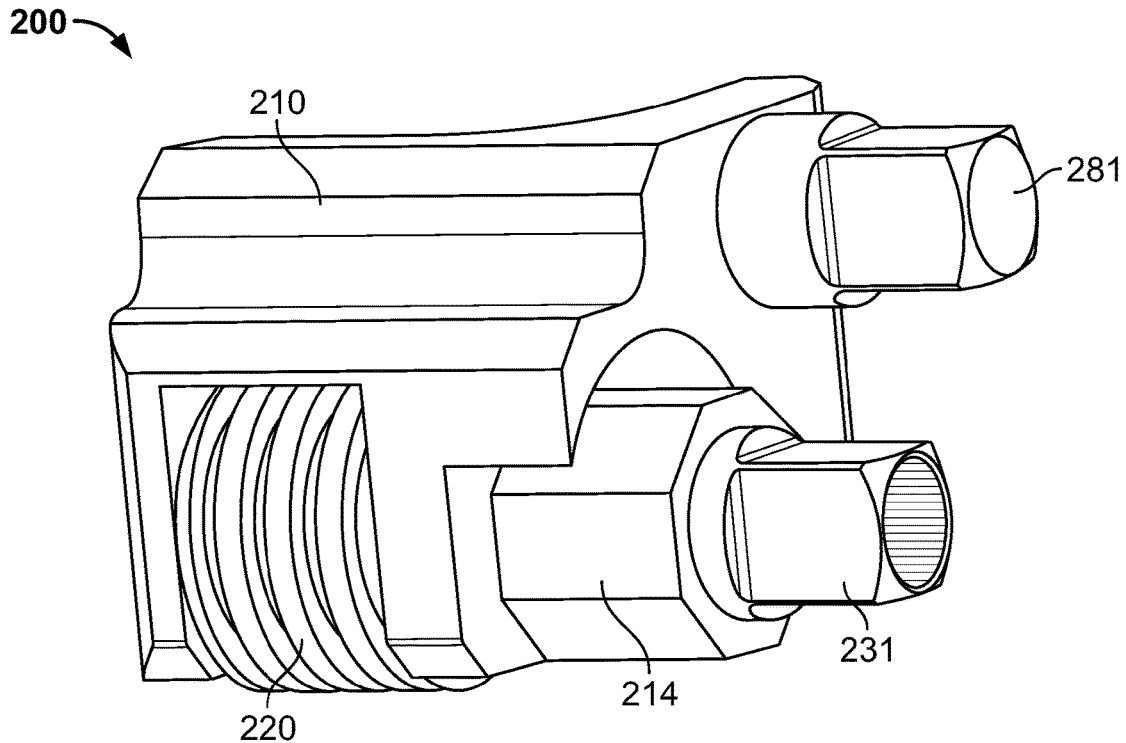
FIG. 4A is a perspective view of a modular attachment member of FIG. 3.
Figure 4B:
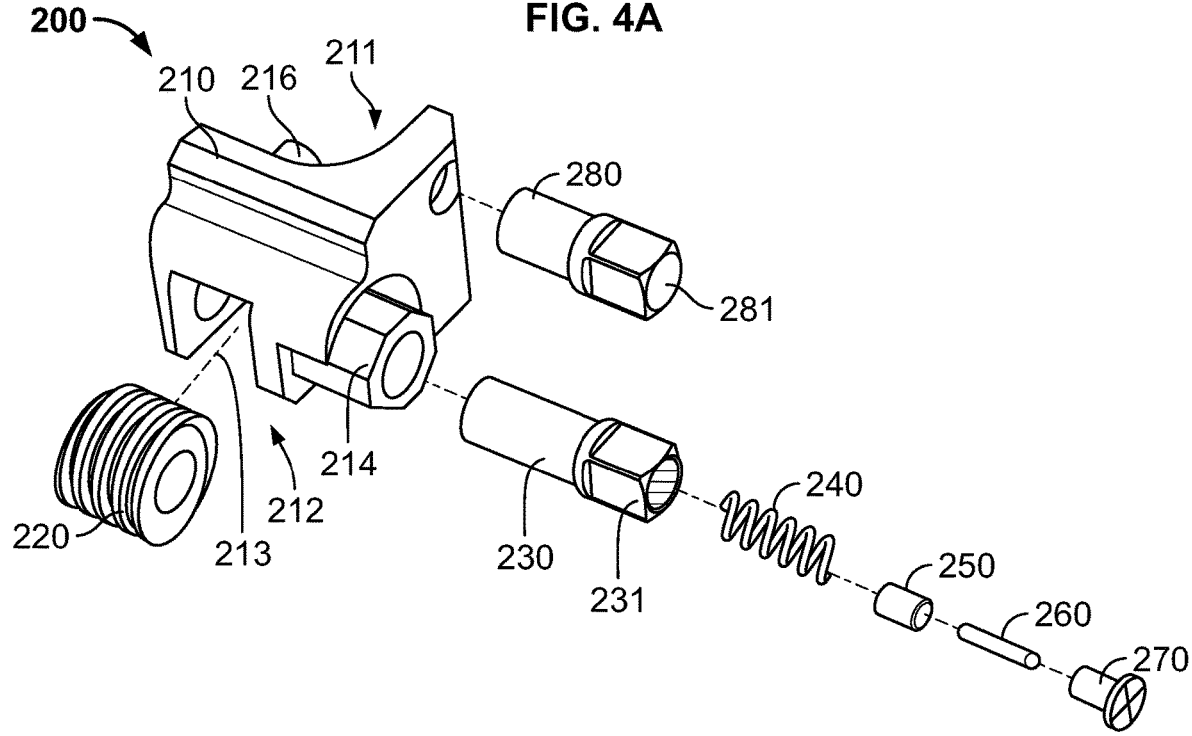
FIG. 4B is an exploded view of the modular attachment member of FIG. 4A.

Attachment piece 200 is shown in greater detail in FIGS. 4A-B. Generally, attachment piece includes a main body 210 having a first contoured side 211 and a second side 212 defining a recess 213. The first contoured side 211 is adapted to be positioned on strut 100 adjacent the actuation mechanism 120. A worm-type gear 220 is adapted to be positioned within recess 213 of second side 212. When attachment piece 200 is attached to strut 100, teeth of the worm gear 220 mesh with gear teeth 122 of actuation mechanism 120, so that rotation of worm gear 220 causes rotation of actuation mechanism 120.

Body 210 of attachment pieces 200 may include a counter-torque feature 214, which may be a piece solidly coupled to, or integrally formed with, body 210 and which may include at least one flat side, for example a hexagonal or octagonal shape. Counter-torque feature 214 may include a bore therethrough leading to recess 213, so that when worm gear 220 is positioned within recess 213, a bolt 230 may be inserted into counter-torque feature 214, with a shaft of bolt 230 extending through worm gear 220 and into an aperture of body 210 on the opposite side of the recess 213 from counter-torque feature 214. When the bolt 230 is assembled to the worm gear 220 and body 210, rotation of the bolt 230 is translated to the worm gear 220. Further, when assembled to the body 210, a head 231 of the bolt 230 may protrude from the counter-torque feature 214. The head 231 of bolt 230 may also include at least one flat surface, such as a square shape, that corresponds to a shape of a recess in a tool, such as a manual or automatic screwdriver type tool. The head 231 of bolt 230 may also include an aperture adapted to receive additional components. For example, in one embodiment, a spring 240 may be situated within the recess of head 231, with an abutment 250 abutting one end of the spring 240. Abutment 250 may be generally any structure sized to fit within the recess of head 231 and to provide a surface against which an end of spring 240 can press, without the abutment 250 getting caught within the internal area of spring 240. The other side of abutment 250 is adapted to provide a surface to bias an RFID tag 260 away from the head 231 of bolt 230 and toward end cap 270. Although described in terms of an RFID tag 260, other suitable near-field wireless identification mechanisms may be used instead of an RFID tag. End cap 270 may take any suitable form and is adapted to be positioned within the recess of the head 231 of bolt 230 and to be secured thereto in order to keep the other components, including spring 240, abutment 250, and RFID tag 260, within the head 231 of bolt 230. End cap 270 may also have an identifying feature, such as a color, number, or other symbol. The purpose of RFID tag 260 and the identifying feature of end cap 270 is discussed in greater detail below in connection with the description of the operation of strut 100 with attachment piece 200 attached thereto.

Figure 4C:
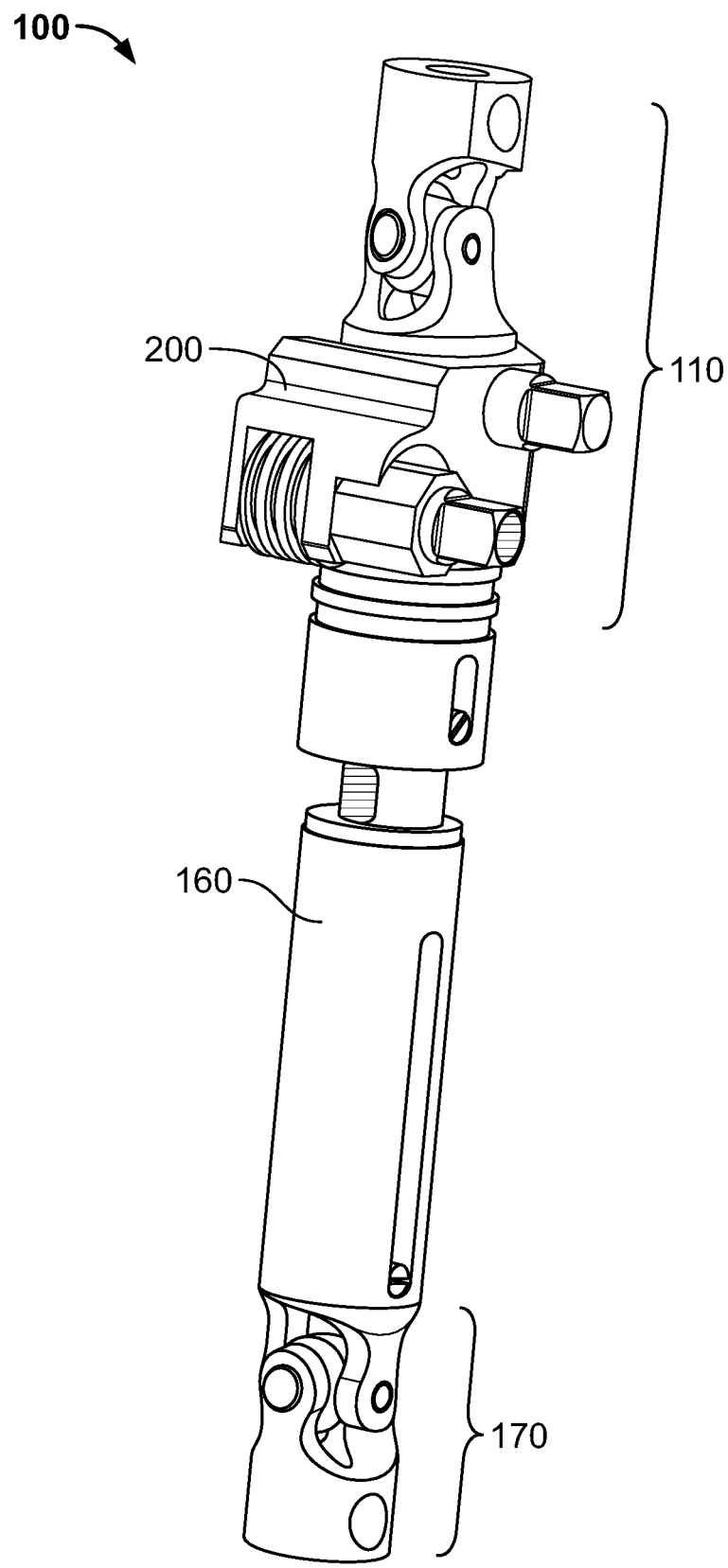
FIG. 4C is a perspective view of the modular attachment member of FIG. 4A coupled to the strut of FIG. 2A.

Attachment piece may include a fastener 280 which may be in the form of a bolt or screw, for example. Fastener 280 includes a head 281 which may include at least one flat surface, such as a square, to mate with an end of a driving tool such as a screwdriver. Fastener 280 may be adapted to be received through an aperture leading to the contoured side 211 of body 210. In order to assemble attachment piece 200 to strut 100, the components of attachment piece 200 other than fastener 280 are first assembled together. A first protrusion 216 of body 210 is inserted into aperture 116 of the first joint 110 of strut 100 (see FIG. 2A). In this position, the teeth 122 of actuation mechanism 120 will mesh with teeth of worm gear 220. Further, in this position, the contoured side 211 of body 210 corresponds to the contoured surface of the distal portion 115 of first joint 110. The fastener 280 is then inserted into its corresponding aperture in body 210, and further into aperture 117 of first joint 110. A screwdriver may be positioned on the head 281 of fastener 280 to screw the fastener into aperture 117, firmly locking the attachment piece 200 to strut 100. The strut 100 with attachment piece 200 coupled thereto is shown in FIG. 4C.

With strut 100 coupled to rings 20, 30 of external fixation system 10, and attachment piece 200 coupled to strut 100, the length of strut 100 may be adjusted using a manual or automated tool. Examples of such tools are described in greater detail in U.S. Patent Application Publication No. 2016/0113681 and Provisional Patent Application No. 62/203,179 titled filed Aug. 10, 2015 and titled "Manual Smart Tool with Clicking Mechanism," the disclosures of which are both hereby incorporated by reference herein. Such driver tools may be motorized or manual, and may include electronic and power components. For example, in one embodiment, the driver tool includes a counter-torque feature that has a corresponding shape (e.g. hexagonal or octagonal) to the counter-torque feature 214 of attachment piece 200. With the counter-torque portion of the driver tool coupled to the counter-torque mechanism 214, a secure connection between the driver tool and the attachment piece is provided. An internal rotating member of the driver may have a corresponding shape to the head 231 of bolt 230 (e.g. square) and be positioned so that, once the counter-torque feature of the driver is positioned over the counter-torque mechanism 214 of the attachment piece, the rotating member of the driver is positioned over the head 231 of bolt 230. At this point, manual rotation of a handle of the driver will cause bolt 230 to rotate, in turn causing worm gear 220 to rotate, actuation mechanism 120 to rotate, and the strut 100 to lengthen or shorten. If the driver tool is motorized, a button may be pressed on the driver to cause the same movement as the manual driver. Whether the driver tool is motorized or not, it may include an RFID reader near the portion that mates with the head 231 of bolt 230. If the driver tool is motorized, the driver tool may only rotate if the driver tool recognizes that it is attached to the correct strut via recognition of the correct RFID tag 160. If the driver tool is manual but includes electronics, the driver tool may display a confirmation that the driver tool is corrected to a particular or desired strut 100. As should be clear from the above description, spring 240 helps push the RFID tag 260 close to the end cap 270 to minimize the distance between the RFID tag 260 and an RFID reader of the driver tool when the driver tool is positioned over the head 231 of the bolt 230.

Figure 5:
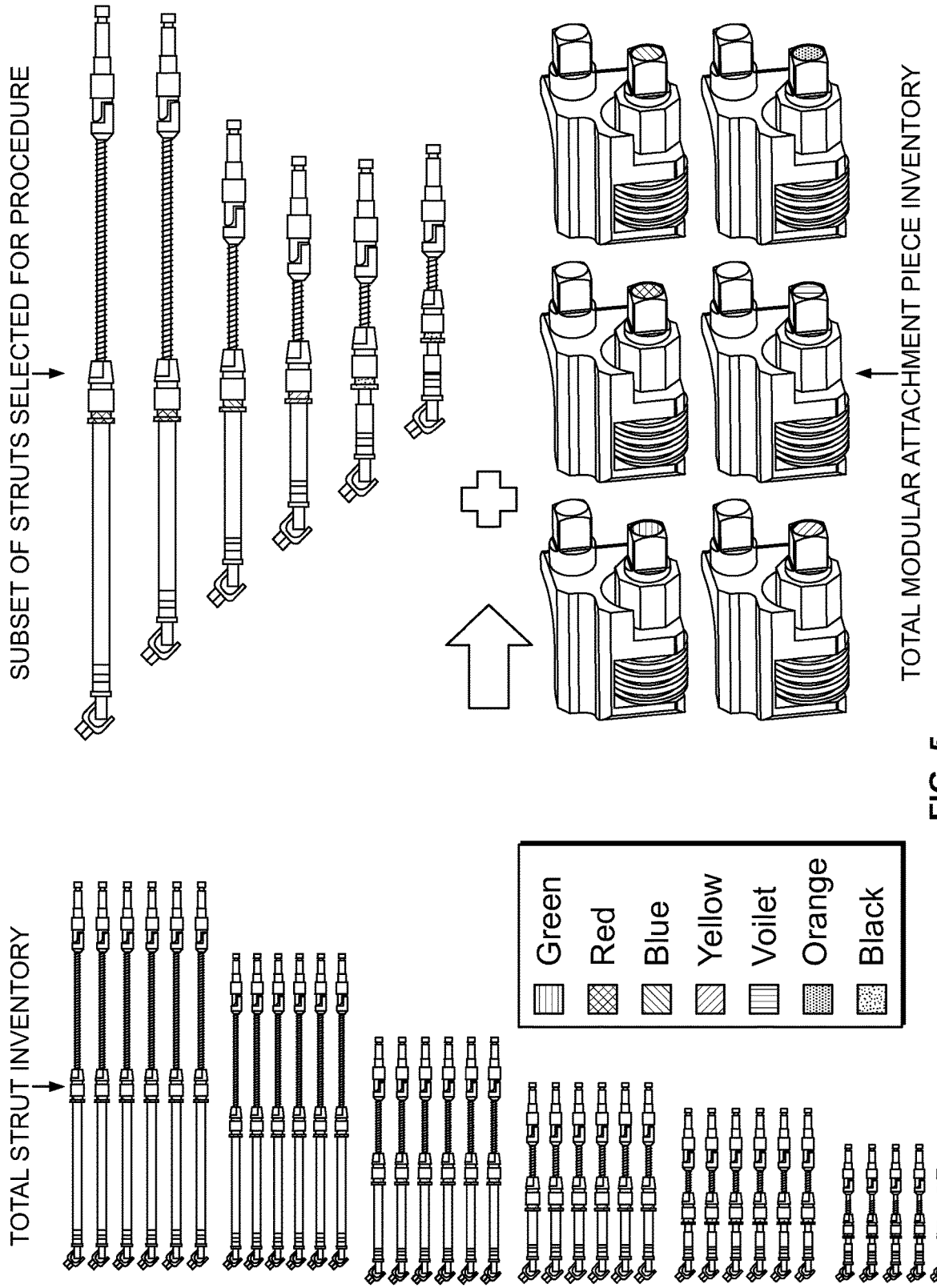
FIG. 5 is a conceptual illustration of an inventory reduction using the modular attachment members of FIG. 3.

Providing attachment piece 200 as a modular item may provide a number of benefits compared to providing the strut 100 with attachment piece 200 integrally coupled to the strut 100. First, it becomes possible to easily manipulate the length of strut 100 manually by hand with actuation mechanism 120, if desired. Second, it should be understood that the exact size and type of struts to be attached to external fixation frame 10 may not be known until the just prior to the struts being coupled to the rings 20, 30 of external fixation system 10. For example, if an external fixation system 10 is intended for use with six total struts, and up to six available strut sizes are available for use, a total of thirty six struts may be provided in a kit along with the other components of fixation frame 10. In this case, thirty-six struts will be required in order to cover any possible combination of the six struts chosen for external fixation frame. If attachment piece 200, along with the particular RFID tag 260 for a given attachment piece 200, was provided integrally formed with or otherwise previously coupled to strut 100, then in this example thirty-six attachment pieces 200 with thirty-six corresponding RFID tags 260 would be required. However, as shown in FIG. 5, the use of a modular attachment piece 200 allows the use of only six attachment pieces 200 total (in a six-strut system), despite the need for thirty-six struts. It should be understood that this may be a significant reduction in inventory requirements and corresponding expenses. Still further, in the case of a malfunction of any electronics in either the attachment piece 200 or a screwdriver tool, the attachment pieces 200 may simply be removed and the correction may continue on a manual basis.

Since each RFID tag 260 should be unique with respect to the other RFID tags 260 in a set of modular attachment pieces 200, it is preferable that the marking or other indicia on each end cap 270 coupled to each bolt 230 matches or otherwise corresponds to a particular strut identifier 140. For example, each of the six positions for a strut on the fixator system may be represented by a color. In one example, a first position for a strut which may be labelled "Position 1" may correspond to a green identifier. Once it is determined that a particular strut 100, for example "Strut 1" is to be used Position 1, a green strut identifier 140 may be snapped onto Strut 1, either before or after attaching Strut 1 to the frame in Position 1. Once Strut 1 is in Position 1 with green strut identifier 140 attached to Strut 1, an attachment piece 200 with a corresponding green-colored end cap 270 may be attached to Strut 1. Because the green identifier corresponds to Position 1, any later identification of Strut 1 will alert a user (for example via a driving tool) that the adjustment for the strut in Position 1 should be made only to Strut 1. During the correction procedure, a user may be instructed to couple a motorized driver tool to "Strut 1" for a scheduled length change. The instructions may include a corresponding green-colored indicator so that patient knows exactly which strut needs to be adjusted. The RFID reader in the driver tool may provide for confirmation upon connection to "Strut 1" and reading the RFID tag 260 that corresponds to "Strut 1." These steps help ensure that a patient is unlikely or unable to adjust the length of a strut other than the particular strut length adjustment called for by the prescribed strut length adjustment plan.

A number of additional benefits may arise from the positioning of the adjustment mechanism 120 and/or the modular attachment pieces 200 just distal to the first joint 110. Since external fixation system 10 may often be used for correcting deformities in bones in the lower extremities, a patient may find it generally difficult to reach down to adjust the length of a strut, depending on where the adjustment mechanism is attached. The disclosed adjustment mechanism 120 is relatively proximal, or in other words closer to the "top" of the external fixation system 10 compared to other components of the fixation system 10. Thus, it may be easier for the patient to reach down to activate adjustment mechanism 120 compared to an adjustment mechanism that is closer to the middle of a strut or even further distal to the middle of the strut. IT should be understood that, even when the struts 100 are lengthened, the adjustment mechanism 120 stays in a substantially constant position with respect to the patient's upper body. Further, if a medical image such as an X-ray is to be taken, the modular attachment pieces 200 may be removed temporarily to provide a better view of the patient's tissue. Often, a bone resection is made in a location that is generally near the middle of the space between rings 20, 30, so it may be beneficial to reduce bulk of struts 100 or related components near the middle of the system 10, since that area may be of highest interest in an X-ray or other image. In other cases, the bone resection is formed in a position that is relatively close to first ring 20. In those cases, struts 100 could be inverted from how they are shown in the Figures, with the attachment piece 200 being positioned closer to the distal ring 30 rather than close to the proximal ring 20 for enhanced visibility during X-ray or other imaging procedures.

The interaction between the worm gear 220 of attachment piece 200 and the actuation mechanism 120 may provide additional benefits. For example, the gear ratios between the worm gear 220 and the actuation mechanism 120 may be controlled to result in a desired torque to change the length of the struts. Further, the gear ratio may provide greater accuracy compared to a traditional strut actuation mechanism including, for example, a screw driver tool that is coupled to a strut along the strut axis where one revolution of the tool results in one revolution of the strut. In such a traditional actuation mechanism, if the tool is rotated too much or too little, there is a one-to-one correlation between the error imparted onto the strut revolution. With an appropriate gear ratio chosen for the worm gear 220 and the actuation mechanism 120, such an error can be reduced if one revolution of the worm gear 220 produces less than one revolution of the actuation mechanism 120, reducing the effect of errors in rotation of the tool.

Figure 6A:
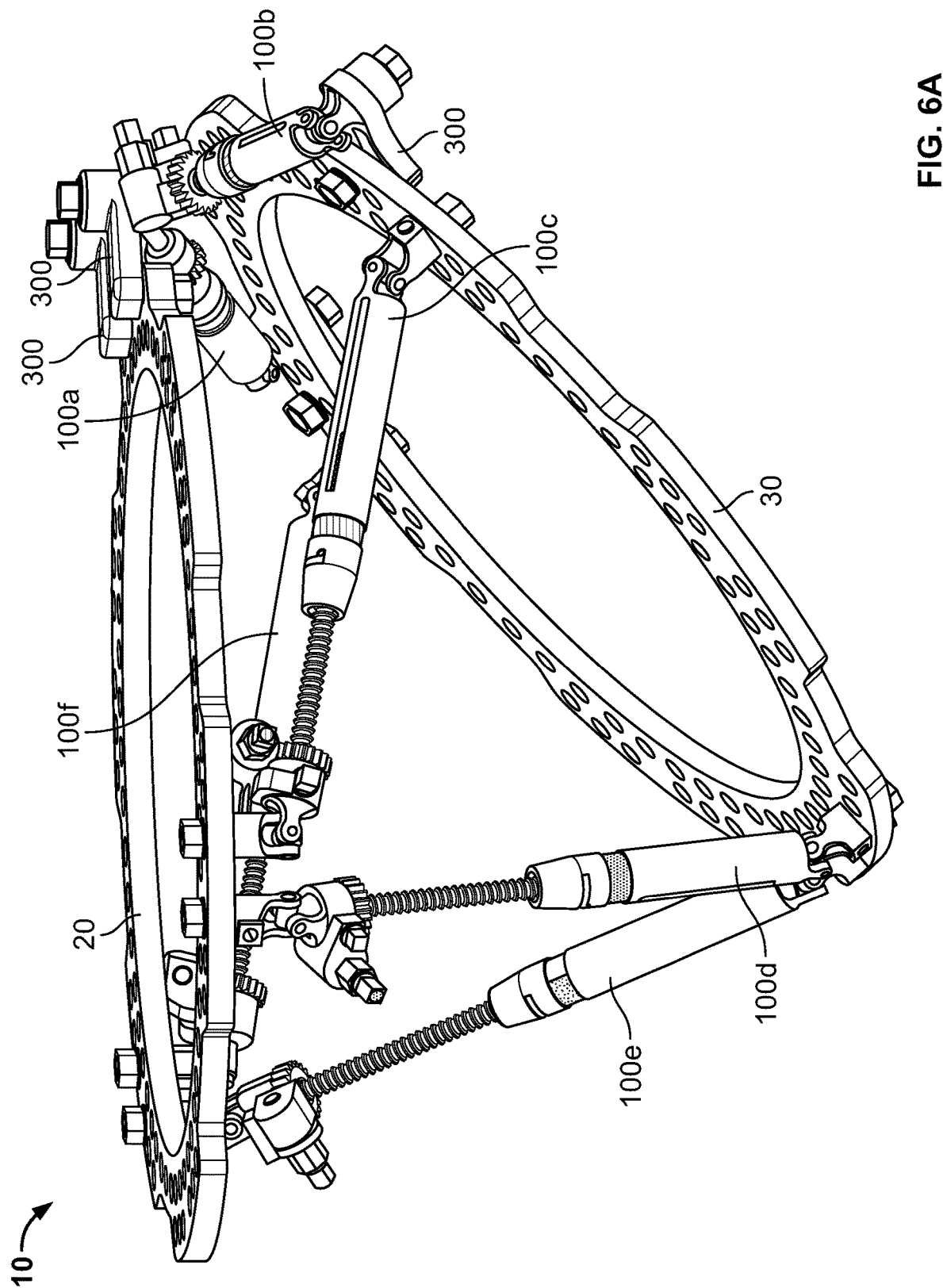
FIGS. 6A-B are perspective views of the external fixation system of FIG. 3 with offset plates attached to certain struts of the system.
Figure 6B:
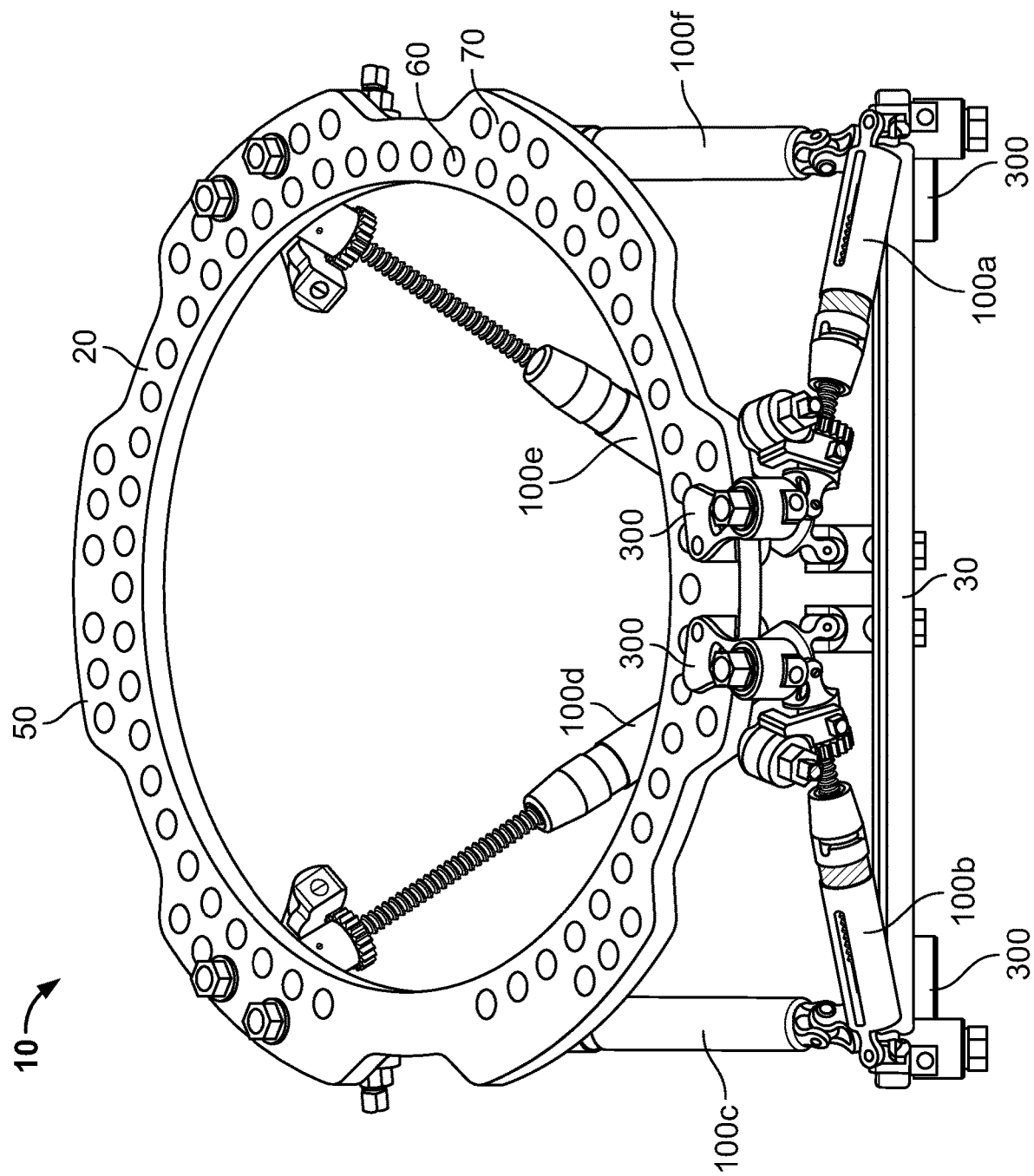

In some deformity corrections using external fixation system 10 (or other similar systems), in order to correct a bone deformity, one or more struts 100*a-f* will need to be adjusted to move one portion of top ring 20 very close to one portion of bottom ring 30. However, if the top of a strut 100 is attached directly to top ring 20 and the bottom of that strut 100 is attached directly to bottom ring 30, there may be a significant amount of structure of strut 100 limiting how close the two rings 20, 30 may be able to get to one another. In order to help solve that problem, one or more offset plates 300 may be used. FIGS. 6A-B illustrate external fixation frame 10 with struts 100*a-f* and six corresponding attachment pieces 200, with both the proximal and distal ends of struts 100*a* and 100*b* each attached to top ring 20 and bottom ring 30 via an offset plate 300, which is shown in greater detail in FIG. 6C.

Figure 6C:
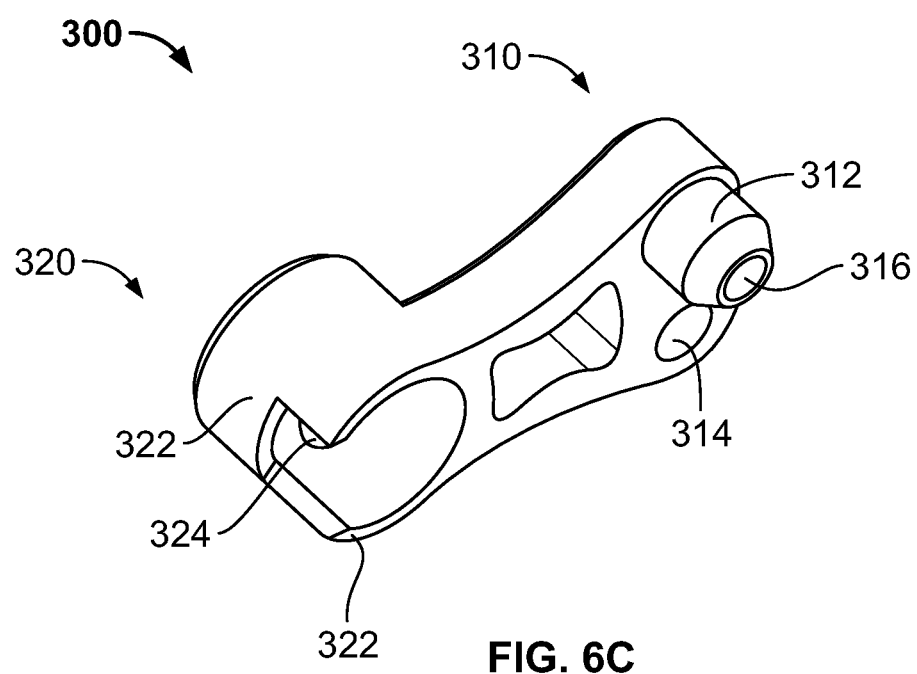
FIG. 6C is a perspective view of an offset plate of FIGS. 6A-B.

Referring now to FIG. 6C, offset plate may include a first end 310 and a second end 320. The first end 310 may be configured to couple to one of the rings 20, 30, and the second end 320 may be configured to couple to an end of a strut 100. In particular, the first end 310 may include an extension 312 and an aperture 314. Extension 312 may be generally cylindrical and shaped to extend into or through an aperture in one of the rings 20, 30. Extension 312 may also include a borehole 316 so that a fastener can pass into an aperture of the ring 20, 30 in which the extension 312 is positioned, the fastener threading into or otherwise fastening the offset plate 300 to the corresponding ring 20, 30. It should be understood that, instead of inserting protrusion 312 into a ring 20, 30, a fastener may be inserted through a ring hole 20, 30 and into aperture 314 to bolt or otherwise secure offset plate 300 to the corresponding ring 20, 30.

When the first end 310 of offset plate 300 is coupled to a ring 20, 30, the second end 320 extends radially outward of the ring 20, 30. The second end 320 of offset plate 300 may include a substantially cylindrical extension 322 having a borehole 324 extending along a longitudinal axis of the extension 322. The cylindrical extension 322 of the offset plate 300 may include a substantially circular rim that defines a generally cylindrical recess, which may be open (as is shown in FIG. 6C) or which may otherwise fully circumscribe borehole 324. With the first end 310 of offset plate 300 coupled to one of the rings 20, 30, the aperture 112 in the proximal portion 111 of first joint 110 is lined up adjacent the borehole 324, with the proximal portion 111 of first joint 110 generally sitting in contact with the circular rim of extension 322, and the aperture 113 being accessible through the open portion of the recess defined by the circular rim. It should be understood that, since the proximal portion 111 of the first joint 110 is substantially identical to the distal portion 175 of the second joint 170, the method of connection the second joint 170 to an offset plate 300 is substantially the same as described in connection with the first joint 110. Although FIGS. 6A-B illustrate that the first and second joints 110, 120 of struts 100*a* and 100*b* are all coupled to offset plates 300, it should be understood that one end of a strut 100 may be coupled to one of the rings 20, 30 directly while the other end is coupled to the other of the rings 20, 30 via offset plate 300.

With the use of one or more offset plates 300 as described above, the structure of the strut 100 coupled to the offset plate(s) 300 is moved out of radial alignment with the structure of the rings 20, 30. As can be seen particularly well in FIGS. 6A-B, this allows for the rings 20, 30 to be positioned closer to one another than would be possible if all struts 100 were directly connected to the top ring 20 and bottom ring 30. This allows for an additional range of motion of the top ring 20 relative to the bottom ring 30 which may not be otherwise achievable. In other words, the closest ring-to-ring distance may be determined by the maximum angle of the joint (e.g. universal joint 110 or 170) at which the struts angle and/or pivot. If a strut is connected directly to a ring, it may have a first maximum pivot angle at that location. If the joints are positioned in between the two rings and are positioned a certain distance from the adjacent ring, the range of angulation of the strut will be limited. However, if the joint pivot points are moved radially outward and out of the way so that they are beyond the rings, the struts are able to angulate a greater degree which may result in closer possible ring-to-ring distance.

Although the invention herein has been described with reference to particular embodiments, it is to be understood that these embodiments are merely illustrative of the principles and applications of the present invention. For example, features described in relation to one particular embodiment may be combined with features of other embodiments described herein. It is therefore to be understood that numerous modifications may be made to the illustrative embodiments and that other arrangements may be devised without departing from the spirit and scope of the present invention as defined by the appended claims.

The invention claimed is:

1. A method of correcting a deformity in a bone of patient using an external fixation system, the method comprising:
    coupling a first support ring to a first segment of the bone;
    coupling a second support ring to a second segment of the bone;
    coupling the first support ring to the second support ring via telescopic struts so that a first end of each strut is coupled to the first support ring and a second end of each strut is coupled to the second support ring, a first joint of each strut being proximate the first end of the strut and a second joint of each strut being proximate the second end of the strut, each strut including a rod having external threads, and a tube having a hollow portion adapted to receive the rod and an engagement feature adapted to engage the external threads of the rod, the rod and the tube both extending between the first joint and the second joint, the rod configured to translate axially relative to the tube, via rotation of the external threads relative to the tube, to adjust a length between the first joint and the second joint;
    wherein after coupling the first support ring to the first segment of the bone, coupling the second support ring to the second segment of the bone, and coupling the first support ring to the second support ring, the external fixation system is in a manual operative condition in which first gear teeth of a first gear fixed to the rod are exposed such that (i) manual rotation of the first gear teeth in a first direction increases the length between the first joint and the second joint and (ii) manual rotation of the first gear teeth in a second direction opposite the first direction decreases the length between the first joint and the second joint; and after assembling the external fixation system into the manual operative condition, coupling a modular attachment member to each of the struts so that second teeth of each modular attachment member engage the first gear teeth of a corresponding one of the struts, so that rotation of the second teeth of one of the modular attachment members causes corresponding rotation of the first gear teeth of the corresponding one of the struts, the gear teeth being separate from the external threads of the rod, the first gear being cylindrical.

2. The method of claim 1, further comprising rotating the second teeth of one of the modular attachment members to change the length of the corresponding one of the struts.

3. The method of claim 2, wherein rotating the second teeth of the one of the modular attachment members includes activating a motor.

4. The method of claim 3, wherein the second teeth are part of a second gear.

5. The method of claim 4, wherein the second gear is a worm gear.

6. The method of claim 4, wherein the motor is housed within a driver tool.

7. The method of claim 6, wherein the driver tool is separate from the modular attachment members, and rotating the second teeth of the one of the modular attachment members includes engaging the driver tool to a bolt of the one of the modular attachment members and rotating the bolt to rotate the second teeth.

8. The method of claim 1, wherein the telescopic struts include six telescopic struts, and the modular attachment members include six modular attachment members.

9. The method of claim 1, wherein the first joint is a universal joint, and the second joint is a universal joint.

10. The method of claim 1, wherein the rod includes a protrusion coupled to an end portion of the rod, the protrusion extending orthogonal to a longitudinal axis of the rod.

11. The method of claim 10, wherein the tube includes an elongate slot extending through inner and outer surfaces of the tube, a portion of the protrusion extending through a portion of the elongate slot.

12. The method of claim 11, wherein the tube includes visual indicia on the outer surface thereof adjacent the slot.

13. The method of claim 12, further comprising comparing a position of the protrusion relative to the visual indicia to determine the length of the strut.

14. The method of claim 1, wherein the first support ring extends along a first ring plane and has a plurality of first apertures extending through the first support ring in a direction orthogonal to the first ring plane, and the second support ring extends along a second ring plane and has a plurality of second apertures extending through the second support ring in a direction orthogonal to the second ring plane.

15. The method of claim 14, further comprising coupling a first end of an offset plate to one of the plurality of first apertures so that a second end of the offset plate extends radially outward of the first support ring.

16. The method of claim 15, wherein coupling the first support ring to the second support ring via telescopic struts includes coupling the first end of one of the telescopic struts to the second end of the offset plate to couple the first end of the one of the telescopic struts to the first support ring.

17. The method of claim 1, wherein coupling the modular attachment members to corresponding ones the struts includes passing a fastener through each modular attachment member and into the corresponding strut.

18. The method of claim 17, wherein the fasteners are bolts or screws.

19. The method of claim 1, wherein each of the struts has a color associated therewith, and each of the modular attachment members has a color associated therewith.

20. The method of claim 19, wherein coupling the modular attachment members to corresponding ones of the struts includes matching the color associated with each modular attachment member to the color associated with each corresponding strut.

* * * * *